United States Patent [19]

Chambers

[11] 4,350,496
[45] Sep. 21, 1982

[54] MEASURING THE AROMATIC REACTIVITY OF A HYDROCARBON COMPOSITION

[76] Inventor: Carlon C. Chambers, 526 20 1/4 Rd., Grand Junction, Colo. 81503

[21] Appl. No.: 273,850

[22] Filed: Jan. 23, 1981

Related U.S. Application Data

[63] Continuation-in-part of Ser. No. 54,690, Jul. 5, 1979, abandoned.

[51] Int. Cl.$^3$ .................... G01N 31/06; G01N 33/26
[52] U.S. Cl. ............................ 23/230 M; 23/230 R; 23/230 HC
[58] Field of Search .......... 23/230 M, 230 HC, 230 R

[56] References Cited

FOREIGN PATENT DOCUMENTS 50-55387  5/1975  Japan ............................ 23/230 HC

OTHER PUBLICATIONS

ASTM D-1017-51 (Reapproved 1968), "Standard Method of Test for Benzene and Toluene by Ultraviolet Spectrophometry".
ASTM D-875-64 (Reapproved 1968), "Calculation of Olefins and Aromatics in Petroleum Distallates from Bromine Number and Acid Absorption".
ASTM D-1019-68, "Olefinic Plus Aromatic Hydrocarbons in Petroleum Distillates".
ASTM D-2267-68, "Aromatics in Light Naphthas and Aviation Gasolines by Gas Chromatography.
ASTM D-1319-70, "Hydrocarbon Types in Liquid Petroleum Products by Fluorescent Indicator Adsorption".
ASTM D-471-72, "Change in Properties of Elastomeric Vulcanizates Resulting from Immersion in Liquids".
ASTM D-936-55 (Reapproved 1968), "Aromatic Hydrocarbons in Olefin-Free Gasolines by Silica Gel Adsorption".

Primary Examiner—Barry Richman
Attorney, Agent, or Firm—Sheridan, Ross & McIntosh

[57] ABSTRACT

The relative aromatic activity of hydrocarbon compositions is determined by measuring and comparing the ability of the hydrocarbon compositions to be sorbed by a polymeric rubber matrix. The aromatic activity is useful in determining chemical, physical and/or biological activity of a hydrocarbon composition.

40 Claims, 1 Drawing Figure

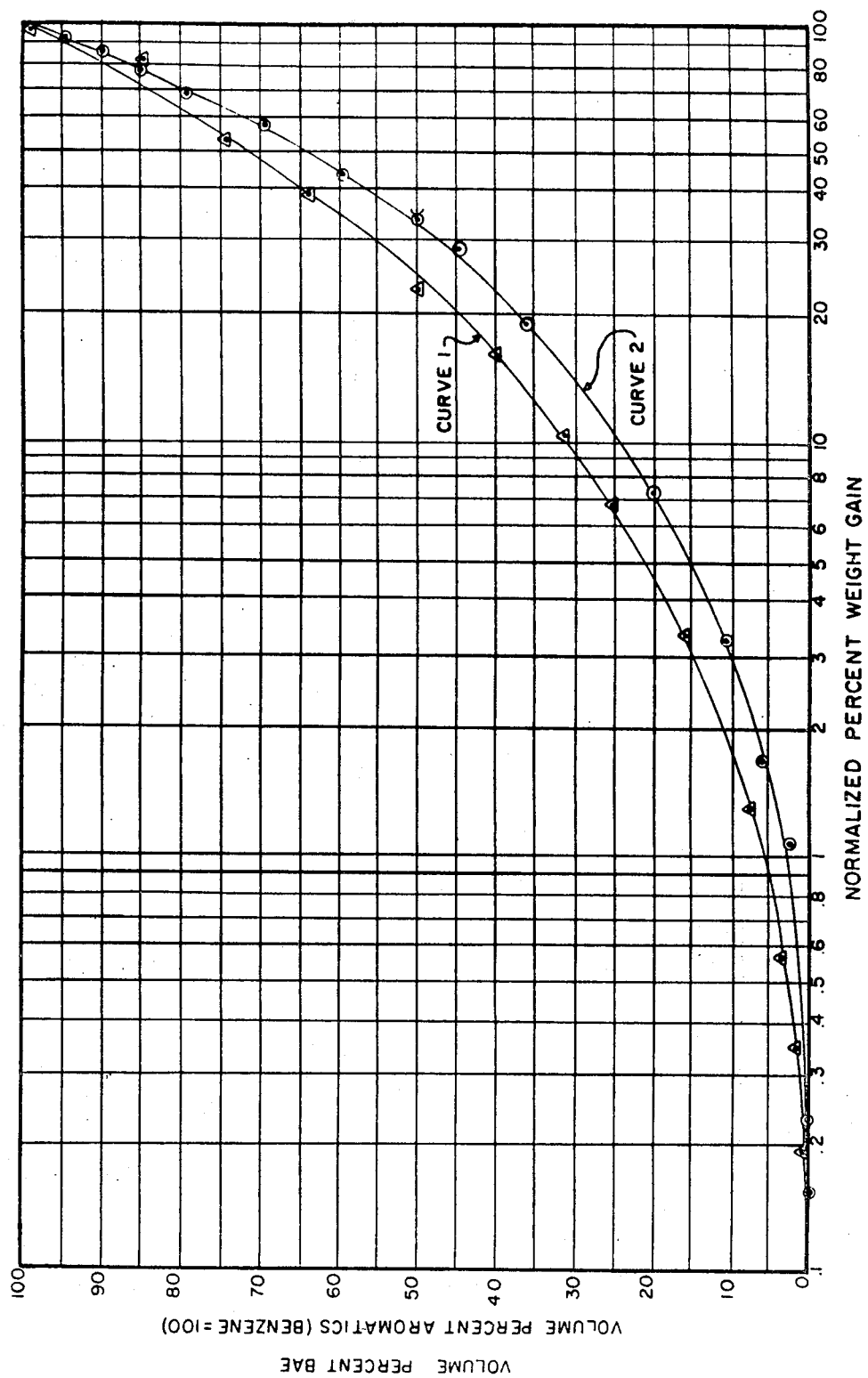

MEASURING THE AROMATIC REACTIVITY OF A HYDROCARBON COMPOSITION

CROSS-RELATED PATENT APPLICATION

This application is a continuation-in-part application of U.S. Ser. No. 054,690 filed July 5, 1979 and now abandoned.

TECHNICAL FIELD

This invention relates to the field of determining the aromatic activity of a hydrocarbon composition. From this determination it is possible to predict the physical, biological and/or chemical interaction or action of the hydrocarbon composition in different types of environments.

BACKGROUND ART

There are several known test methods for determining various types of characteristics of hydrocarbon compounds, many of which are published by the American Society for Testing and Materials (ASTM). Many tests are directed toward determining the aromatic content of a liquid hydrocarbon, for example ASTM D2267-68 and ASTM D936-55 both test for aromatics in gasolines and ASTM D1017-51 tests for the presence of toluene and benzene. ASTM D875-64 (1968) and ASTM D1019-68 additionally test for the presence of olefins in petroleum distillates and ASTM D1319-70 tests for the presence of saturates, nonaromatic olefins and aromatics in petroleum fractions by fluorescent indicator absorption. Most of these tests are very long and involved, as an example, the D1319-70 test takes more than three hours to test one sample. Moreover, there is no direct correlation between the relative amounts of aromatics, olefins and saturates in a compound which allows one to predict the activity of the compound.

In the last few years, the environmental impact, e.g., potential toxicity and pollution problems, of known and new compounds has become of great interest and concern. In fact, the Federal Government and several state governments have promulgated regulations relating to the potential toxicity of compounds which are based on threshold limit values, e.g., the threshold amount of compound in terms of milligrams per cubic meter of air which will cause toxicity, and acceptable amounts of products which can be airborne based on the compound's photochemical activity. These values are generated for each specific chemical compound and chemical mixture and involve very time consuming techniques. Absent the specific testing of each hydrocarbon compound and hydrocarbon mixture, there is no way of predicting the toxicity or air pollution potential of any given hydrocarbon mixture.

It is known that hydrocarbons have the ability to be absorbed by rubber. For example, the ASTM D471-72 test for change in properties of elastomeric vulcanizates resulting from immersion in liquids does measure the change in weight or volume of the test elastomer specimen caused by immersion in a liquid. The purpose of the test, however, is to measure the effect of a particular liquid on a particular elastomer, not to measure the activity of the liquid. There has been no recognition that the phenomenon of absorption of a hydrocarbon by a rubber matrix may be used as a quantitative assay of a hydrocarbon compound which will enable one to predict the activity of the compound in a number of different circumstances. The present invention relies on this absorption phenomenon to determine the aromatic activity of a hydrocarbon which is predictive of a wide variety of chemical and/or physical activities of the hydrocarbon. Additionally, the test is fairly inexpensive, is applicable to liquid, vapor, solid and semisolid hydrocarbons and several samples can be run simultaneously in, for example, a three hour time period.

DISCLOSURE OF THE INVENTION

The relative aromatic activity of hydrocarbon compositions is determined by measuring and comparing the ability of the hydrocarbon compositions to be sorbed by a polymeric rubber matrix. One embodiment of the invention comprises measuring the ability of the hydrocarbon composition under standardized conditions to cause a short term weight gain of a polymeric rubber matrix when in physical contact with the rubber matrix and comparing this value to a predetermined aromatic activity of a standard mixture of hydrocarbons to obtain the aromatic equivalent (AE) value of the hydrocarbon composition. Another embodiment comprises measuring the short term weight gains in a polymeric rubber matrix under standardized conditions caused by two or more hydrocarbon compositions and comparing the values to determine the relative aromatic activity of the compositions to each other. In this embodiment at least one of the compositions can be a known aromatic compound, such as benzene. The resulting value from comparing the values of the other compositions to the value of benzene, in any embodiment, is generally termed herein as the benzene aromatic equivalent, as described more fully hereinafter.

Any means used to determine the aromatic activity of a hydrocarbon composition, by comparison, may be used whether it be electronic, such as a computer, mechanical, such as a cam, a curve, an equation, etc. For example, the weight gain of a test coupon caused by a hydrocarbon composition may be used in conjunction with the following formula to obtain the aromatic equivalent (AE) value:

$$Y = X^{\alpha + \beta \ln x}$$

wherein:
- Y = fractional volume percent AE
- X = fractional percent of a corrected and normalized weight gain of a test coupon
- $\alpha$ = coefficient
- $\beta$ = coefficient
- ln = natural logarithm Prior to obtaining the AE value of the hydrocarbon, the weights of the rubber coupons should be corrected to a standard weight, e.g., 1.0000 grams and, if necessary, the exposure time of the rubber coupon to the hydrocarbon should be corrected to a standard time and then the weight gains caused by the hydrocarbons should be normalized.

The significance of a benzene aromatic equivalent value is related to the fact that benzene is recognized as being the most active of the aromatic hydrocarbon series. Because of this, it also has the highest solvency power and the highest human toxicity rating of the same series of hydrocarbons. This series of hydrocarbons is defined as the benzenoid series of aromatic hydrocarbons which is based on the unsaturated, six carbon benzene ring molecular structure. Thus, the BAE value, as well as the AE value to another aromatic compound, is useful in predicting various physical, biological and/or chemical activities of hydrocarbons. For example, it is useful in the determination of: the relative or average toxicity of pure hydrocarbons and mixtures of hydrocarbons; the presence of like boiling range aromatic impurities in high purity aliphatic hydrocarbon process streams; the presence of like boiling range aliphatic hydrocarbon impurities in high purity aromatic hydrocarbon streams; dissolved aromatic hydrocarbon contamination of water, an aqueous stream containing inorganic compounds and/or an aliphatic hydrocarbon stream; probable compatibility or stability of a substance within a mixture; compliance with product or process stream specifications defined with respect to AE values; and compliance for a given product with air pollution regulations.

DESCRIPTION OF THE FIGURE

The FIGURE is a graph of two different curves showing weight gain caused by mixtures of calibration liquids. Curve 1 utilizes Tiechert 350 (a low vapor pressure, nonaromatic hydrocarbon solvent mixture manufactured by the Tiechert Techtonics Company) as the zero calibration point liquid, benzene is the 100 calibration point liquid and the intermediate points are representative of weight gains caused by mixtures of these calibration liquids. N-decane is the zero calibration point and benzene is the 100 calibration point of Curve 2.

BEST MODE FOR CARRYING OUT THE INVENTION

For the purposes of this invention, the aromatic activity of a hydrocarbon composition is defined as the ability of the hydrocarbon composition to cause a short term weight gain and/or swelling of a polymeric rubber matrix, when in physical contact with the rubber matrix. The relative aromatic activity is determined by comparing the weight gains and/or swellings caused by more than one hydrocarbon composition. The aromatic equivalent (AE) value of a hydrocarbon composition is defined as the ability of the hydrocarbon composition to cause a short term weight gain and/or swelling of a polymeric rubber matrix, when in physical contact with the rubber matrix, that is equivalent in action to a known volume percent of an aromatic calibration compound, such as benzene, when mixed with a diluent calibration compound having low aromatic activity, e.g., a nonaromatic hydrocarbon, preferably an aliphatic hydrocarbon, such as n-decane or isooctane. Within the defined limits of the test, a 100 volume percent concentration of the aromatic calibration compound gives an AE value of 100 and a 100 volume percent concentration of the diluent calibration compound gives an AE value of zero.

It is preferred that each of the calibration compounds be pure compounds, not mixtures, and that the diluent calibration compound have a vapor pressure no greater than that of the aromatic calibration compound. Although calibration compounds which are mixtures or diluent calibration compounds having vapor pressures greater than the aromatic calibration compound may be used, the sensitivity of the test will not be as great. Any of a number of aromatic calibration compounds can be used as the aromatic calibration compound, for example, benzene, toluene, chlorinated aromatic compounds and naphthene. The particular aromatic calibration compound selected will be dependent upon the purpose for determining the AE value of a hydrocarbon composition. Since benzene is readily available, many of its physical and chemical properties are known and it has a high aromatic activity, it is a convenient aromatic calibration compound to use. Generally, the lower the aromatic activity of a diluent calibration compound, the more preferred it is. For example, isooctance is preferred over n-decane because it causes a smaller weight gain in a polymeric rubber matrix.

The AE value is determined by comparing the corrected and normalized short term weight gain of a polymeric matrix caused by a hydrocarbon composition to a predetermined aromatic activity of a standard mixture of known hydrocarbon calibration compounds. Predetermined aromatic activity values and predetermined aromatic activity of a standard mixture refer to any data which establish corrected and/or normalized weight gains of a polymeric matrix by known hydrocarbon compositions. The predetermined aromatic activity of a standard mixture may be utilized in the form of a curve, an equation, a mechanical form, such as a cam, an electronic form, such as a computer, etc.

The invention is applicable to a wide variety of hydrocarbon compositions which are defined as hydrocarbons and hydrocarbon mixtures including hydrocarbons which have been nitrated, sulfonated, oxygenated and/or halogenated. It is especially applicable to unsaturated hydrocarbons, preferably unsaturated hydrocarbon ring structures, for example, those of the benzenoid series, naphthalene and anthracene. Totally saturated paraffinic hydrocarbons having a vapor pressure less than that of an aromatic compound will give an AE value of zero or close to zero. For the purposes of this invention, it is not necessary to know the analytical structure or composition of the hydrocarbon being tested. The hydrocarbon may be a solid, semisolid, liquid or a vapor. If it is a solid or a semisolid, it is first dissolved in a solvent prior to measuring its sorption by a rubber coupon. The AE values of solid, semisolid and liquid hydrocarbons are determined from a predetermined aromatic activity of a standard mixture of liquids; whereas, the AE values of hydrocarbon gases are determined from a predetermined aromatic activity of a standard mixture of vapors.

The polymeric rubber coupons useful in this analytical technique consist of synthetic rubbers which are not readily dissolved by either the calibration compounds of the standard mixture used in establishing the predetermined aromatic activity or by the hydrocarbon compositions being tested. The synthetic rubbers must have the ability to exhibit a preferential sorption between aliphatic and aromatic hydrocarbons. Generally, they will exhibit a preference for aromatic hydrocarbons. However, if a synthetic rubber exhibits a preference for the sorption of aliphatic hydrocarbons, then the technique is used to show the aliphatic activity equivalence of the hydrocarbon composition and the AE value will be an inverse measure of the aliphatic activity equivalence. Viton ®️ (trademark of the duPont Company), a copolymer of vinylidene fluoride and hexafluoropropylene, and H-1262, a blend of hycar rubber (polyacrylic rubber) and styrene butadiene rubber manufactured by the Mercer Rubber Company of Trenton, N.J., are examples of suitable rubbers for the test coupons. JH-21 (manufactured by the Mercer Rubber Co.), a 100 percent polyacrylic elastomer, is a preferred synthetic rubber. Neoprene and Hypalon ®️, a chlorosulfonated polyethylene elastomer, are not suitable rubbers for determining BAE values inasmuch as they are partially dissolved by benzene.

To determine the weight gains of the rubber test coupons caused by the hydrocarbons, one rubber coupon of a standard weight range is placed in an enclosed container in physical contact for a specific time period with a specific amount of the hydrocarbon composition being tested. Immediately thereafter, the coupon is separated from the hydrocarbon composition, blotted dry, if necessary, and weighed at a specified time, preferably within thirty seconds of its exposure to the atmosphere. When the hydrocarbon composition is a liquid or a solid or semisolid dissolved in a liquid solvent, the container may be a flask. When the hydrocarbon composition is a gas, a flow cell may be used as the container and a specific amount of the hydrocarbon may be injected or aspirated through the cell for the specified time period.

The standardized rubber coupons are prepared from sheets of specially compounded rubber as described above. These sheets should be of uniform thickness of from about 0.0625 (0.16 cm.) to about 0.125 (0.32 cm.) inches thick and cut into strips that are about 0.5 inches (1.3 cm.) wide. These strips are then cut into lengths which will give a coupon weight of $1.0 \pm 0.25$ grams. To obtain standardized results, all of the AE test results are standardized, for example, to a 1.0000 gram rubber coupon. The percentage correction required for tests in which the coupon weight is other than 1.0000 grams is defined by the following curve fitting equation:

$$X = a_1 Y + a_o$$

wherein:
X = the percentage difference of results from results that would have been obtained had the coupon weight been 1.0000 grams.
Y = actual coupon weight in grams.
$a_1$ = a constant
$a_o$ = a constant When H-1262 is used as the rubber coupon, $a_1$ is $-18.2550$ and $a_o$ is 19.1350. The corrected weight of the coupon for each test ($X_1$) is obtained by adding or subtracting the indicated correction to obtain the weight corrected $X_1$ which is $X_{1w}$.

The test is generally standardized using a two hour exposure time. Different exposure times may be used; however, the results will differ from those obtained from a standard two hour test. Thus, the results from a test of a different time period must be corrected to the $X_1$ of a two hour test by applying the equation shown below. This will allow the determination of the percentage difference of the test time from the two hour standard based on the standardized coupon weight. This correction is determined by the same curve fitting equation:

$$X = a_1 Y + a_o$$

wherein:
X = the percentage difference of the results from the results that would have been obtained with a two hour test.
Y = the percentage difference of the test time from the two hour standard.
$a_1$ = a constant
$a_o$ = a constant When H-1262 is used as the rubber coupon, $a_1$ is 0.5620 and $a_o$ is $-0.0800$. The indicated correction is applied in the same manner as the weight correction to the $X_1$ or $X_{1w}$ of the applicable test to obtain a corrected $X_1$ ($X_1$ corrected for time is $X_{1T}$, or corrected for time and coupon weight is $X_{1TW}$).

The corrected weight gain and/or swelling of a polymeric rubber matrix caused by the standard mixture may cause the AE value of the aromatic calibration compound to deviate from a value of 100. Therefore, so that comparative values may be obtained, the weight gain percentages of all samples after being corrected should be normalized with respect to the predetermined aromatic activity of a standard mixture in accordance with the following formula:

$$X_n = (X_3 - b)\left(\frac{100}{X_2 - b}\right)$$

wherein:
$X_n$ = normalized weight gain percentage
$X_3$ = the corrected weight gain percentage (time and/or weight)
$X_2 = X_3$ of the 100 percent calibration test
$b = X_3$ of the 0 percent calibration test It is the normalized weight gain percentage ($X_n$) which is used in determining the final AE value of a hydrocarbon composition.

The AE value of each hydrocarbon composition is obtained by comparing the corrected and normalized weight gain caused by the hydrocarbon composition to a predetermined aromatic activity of a standard mixture. The predetermined aromatic activity of a standard mixture is established by performing the above described technique on a zero percent standard, i.e., a diluent calibration compound, on a 100 percent standard, i.e., an aromatic calibration compound, and various combinations of the two. The predetermined aromatic activity values are readily utilized in the form of a curve which may be established by plotting the corrected and normalized results of these tests on three cycle semilog graph paper with corrected and normalized percentage weight increase on the X axis (log scale) and the volume percent aromatic equivalent (AE) on the Y axis (linear scale).

The predetermined aromatic activity values are standardized not only with respect to the form of the compound being tested, i.e., liquid or vapor, but also with respect to batches of reagents, volume of compound tested, time of contact between the compound and the rubber coupon, etc. Thus, when any parameter of the testing technique is altered, it is best to generate new predetermined aromatic activity values or at least run comparative samples reflecting this change in parameter so that if this change affects the AE value, its effect will be known. Even when predetermined aromatic activity values of standardized conditions are already established, if samples are tested infrequently, it is a good practice to include a zero percent, a 100 percent and an intermediate percentage calibration tests with each test series. This will give confidence as to the results by ensuring that nothing has changed the effectiveness of the coupons or calibration reagents.

When the predetermined aromatic activity of a standard mixture is used in the form of a curve, the curve is defined by an equation of the following form:

$$Y = X^{\alpha + \beta \ln x}$$

wherein:
Y = fractional volume percent AE
X = fractional percent of a corrected and normalized weight gain of a test coupon
α = coefficient
β = coefficient
ln = natural logarithm When this equation is used, percentages must be expressed as their decimal equivalents of a fraction.

The coefficients are defined by a standard linear least squares regression curve fit of:

$$\left(\frac{\ln Y}{\ln X}\right) \text{ vs. } \ln X$$

in the form of $y = \beta x + \alpha$, wherein:

$$y = \frac{\ln Y}{\ln X}$$

$$x = \ln X$$

$$\beta = \frac{\Sigma xy - \frac{\Sigma x \Sigma y}{n}}{\Sigma x^2 - \frac{(\Sigma x)^2}{n}}$$

$$\alpha = \bar{y} - \beta \bar{x}$$

$$\bar{y} = \frac{\Sigma y}{n}$$

$$\bar{x} = \frac{\Sigma x}{n}$$

n = number of inputs and wherein X and Y are values taken from the predetermined aromatic activity of a standard mixture of from a plotted curve of those aromatic activity values. The above equation, $y = \beta x + \alpha$, is the form used to derive the constants for the weight and time corrections, $X = a_1 Y + a_o$, referred to previously, after X and Y are interchanged and $a_1 = \beta$ and $a_o = \alpha$.

When the curve is that of n-decane and benzene using a polymeric coupon of H-1262 rubber, i.e., curve 2 of the FIGURE, α is 0.567828078 and β is −0.040988750. Although this equation does not represent an exact fit of a curve of predetermined aromatic activity of a standard mixture, it is sufficient to define an AE. For example, with respect to Curve 2 of the FIGURE, the deviations are small with the greatest variance being 3.1 BAE units and the largest percentage errors are associated with Y being less than or equal to 0.5. If more accurate results are required, then the predetermined aromatic values should be used directly, e.g., in the form of a curve, to determine the AE value or a better equation which more accurately fits the curve should be derived. Similar equations can be readily derived, including ones which may more accurately fit the curve.

The tests should always be run with a standardized volume of either a liquid sample or a vapor sample inasmuch as different volumes have a significant effect which is nonlinear. Therefore, all sample volumes should be the same.

Temperature does not appear to be critical and may vary over a fairly wide range. It is preferred that the temperature be in a range from about 65°–80° F.

The sensitivity of the AE test can be varied by many parameters. Examples include, changing the weight of the rubber coupon and/or its thickness, changing the surface to volume ratio of the rubber coupon or changing the test time interval. For example, a coupon of greater weight will result in a smaller percentage weight increase. Conversely, as the weight of the coupon is decreased, a greater weight percentage increase will be reflected. A decrease in the thickness of a coupon allows the hydrocarbon composition to go through the coupon faster so the weight gain and/or swelling occurs quicker. Similarly, as the test time interval is increased, the potential weight gain caused by the compound being tested increases. The sensitivity of the test will generally increase as the surface area of the rubber coupon increases for a given volume of coupon.

When the hydrocarbon composition being tested is a solid or a semisolid which necessitates its dissolution in a solvent, the AE (Y) that is obtained will be of the blend ($Y_b$). To calculate the AE of the hydrocarbon or hydrocarbon mixture ($Y_x$) the following equation is used:

$$Y_x = \frac{(V_b Y_b) - (V_s Y_s)}{V_x}$$

wherein:
$V_b$ = volume percent of the blend, assumed to be 100 percent
$V_s$ = volume percent of the solvent in the blend
$V_x$ = volume percent of the unknown in the blend
$Y_b$ = volume percent AE of the blend
$Y_s$ = volume percent AE of the solvent
$Y_x$ = volume percent AE of the hydrocarbon or hydrocarbon mixture, and wherein $Y_b \geq V_s$.

In the case of a solid or semisolid hydrocarbon, when the solvent used is other than one used in the calibration composition of the predetermined aromatic activity, a sample of the pure organic solvent used to dissolve the solid or semisolid must be included in the test series so that its AE can be determined. This will allow for the AE of the solid or semisolid hydrocarbon composition to be determined.

Similarly, the relative aromatic activity of two or more hydrocarbon compositions can be determined. Each hydrocarbon composition is exposed to the same kind of rubber coupon under standardized conditions. The time of exposure and weight of each of the rubber coupons should be corrected, if necessary, and normalized, and the weight gains of the hydrocarbon compositions corrected accordingly. The hydrocarbon composition which causes the greatest weight gain will exhibit the greatest aromatic activity. Conversely, the hydrocarbon which causes the smallest weight gain will exhibit the least aromatic activity.

Because not all aromatic type molecules have the same activity as pertains to physical, chemical or biological actions, the significance of the measurement of the aromatic equivalent value of a hydrocarbon composition lies in the fact that it is a very good measure of aromatic activity. The higher the AE value, the more aromatic activity the composition exhibits. This measurement of aromatic activity is of significance in many different types of applications. For example, it is of value in determining or predicting the compatibility of organic materials, detecting aromatic hydrocarbon impurities, setting and determining specifications for product process streams, determining the presence of aromatic impurities in water, aqueous solutions and aliphatic streams, predicting the relative biological activity and toxicity of aromatic hydrocarbons in human beings or animals and predicting the photochemical activity of an aromatic hydrocarbon as an air pollutant.

AE values can be very useful in the research and development of new and useful products made from blended or reacted organic materials. One of the problems in developing such products is that not all organic materials are compatible with one another. AE values are useful in determining the stability and compatibility of hydrocarbon compositions with each other. The AE values of known hydrocarbon compositions with known desired characteristics are determined empirically. The AE values of these hydrocarbon compositions are then used to establish AE ranges indicative of stable and compatible mixtures of the type of product sought, thereby allowing one to predict the stability of other known and unknown hydrocarbon compositions when blended. The compatible AE value ranges will vary depending upon the type of product being manufactured, its desired properties and the type starting materials used. The use of AE values is especially useful when blending one or more hydrocarbons having unknown compositions.

For example, if a paraffinic hydrocarbon is blended with another hydrocarbon which has a high asphaltene content, the asphaltenes will precipitate and the resulting liquid phase is viscosity unstable. Since the paraffinic and/or asphaltene content of the blended hydrocarbons may not be known, these effects may not be recognized immediately and may result in the inadvertant manufacture of a product that will have a very short shelf life, i.e., a product which will precipitate solids and thicken. Stability in such blends depends on selecting compounds that will be compatible.

When selecting a hydrocarbon composition to be mixed with a hydrocarbon mixture known to contain asphaltenes, e.g., asphalt, pitch and gilsonite, the AE value of the hydrocarbon composition should be at least equal to or greater than the AE value of the hydrocarbon asphaltene mixture. The greater the percentage of asphaltenes in the mixture, the greater the AE value of the hydrocarbon composition should be over that of the asphaltene mixture. For example, if the mixture contains 5 percent or 10 percent asphaltenes, the BAE value of the hydrocarbon mixture being added should be about 100–110 percent and about 100–120 percent, respectively, of the BAE value of the asphaltene mixture. The technique is useful in the formulation of a number of products containing asphaltenes, including, pavement sealers, ground sealers, rubberized asphalt membranes, pond liners and water stop coatings.

BAE values can also be of use in predicting the compatibility of elastomeric and rigid polymers with other hydrocarbon materials. As an example, solvents used to dissolve elastomeric polymers and some rigid polymers should have a BAE value of from about 37 to about 115. Outside of these ranges there is no significant dissolution of the polymers. The optimum BAE value of a solvent for polystyrene is about 95; polybutadiene is about 66; polyisoprene is about 52; polyethylene/butylene is about 46; and polysulfide is about 97. There is also a certain range of aromatic activity that asphalt hydrocarbons must have to be able to achieve maximum levels of performance from styrene butadiene type elastomers in asphalt based hot melts. The desired aromatic activity is a BAE value of from about 28 to about 42. This value is dependent upon the asphaltene content of the asphalt. When the asphaltene content is lower, a BAE value of about 28 is preferred; whereas, when the asphalt contains 20 percent asphaltenes, a BAE value of about 42 is preferred. Below this range of compatibility there will be a phase separation; and above it, there will be no beneficial difference in blend properties due to polymer addition. It is possible to empirically predict the AE value range for solvents of other elastomers and of hydrocarbon compositions to be blended to form a hot melt of another type.

The determination of AE values is also helpful in checking product purity or contamination of pure chemicals or mixtures. For example, AE determinations can detect like boiling range aromatic impurities in high purity aliphatic hydrocarbon process streams or they can indicate like boiling range aliphatic hydrocarbon impurities in high purity aromatic hydrocarbon streams. A stream containing an aromatic impurity will have a higher AE value than the pure aliphatic hydrocarbon stream. Similarly, an aliphatic hydrocarbon, an aqueous and/or inorganic impurity is indicated by a lower AE value than the AE value of the high purity aromatic hydrocarbon stream alone.

Additionally, dissolved aromatic hydrocarbon contaminants can be detected in water through the use of AE values. Water will have a AE value of 0 and the presence of an aromatic hydrocarbon contaminant will cause the AE value to be greater than 0. A somewhat related use of AE values is their use to define the specifications of a product or process stream. A deviation from an established AE value for a process stream would be indicative of a substandard product or process stream.

Air pollution has become a major concern of both the Federal Government and the state governments. Very often, a compound's propensity to cause air pullution is determined by its photochemical reactivity. Limited data indicates that the BAE values of aromatic hydrocarbons have an inverse relationship to the photochemical reactivity of aromatic hydrocarbons. In other words, the higher the BAE value of an aromatic compound is, the lower its photochemical reactivity is.

Moreover, a direct relationship has been found between the recited toxicity of hydrocarbons and the hydrocarbons' BAE values. Compounds having higher BAE values are more toxic than compounds with lower BAE values, at least with respect to toxicity caused by absorption of the compound through the skin or by inhalation. By correlating the BAE values and toxicity values, e.g., threshold limit values, of hydrocarbon compositions whose toxicity is known, it is possible to determine the toxicity of a hydrocarbon composition, whose toxicity is not known, by applying the correlation factor to the BAE value of the hydrocarbon composition. The BAE values are especially useful in the formulation of liquid products which in liquid or vapor form will comply with various health and air pollution regulations.

EXAMPLE 1

Rubber coupons were prepared from samples of H-1262 synthetic rubber which were of a uniform thickness of between 0.625 and 0.125 inches and cut into strips of 0.5 inches wide and a length such that each coupon had a weight of from between 0.7 and 1.0 grams. To prevent contamination, the rubber coupons were handled with gloves and they were stored in airtight containers until used. Exactly 25 milliliters of each liquid to be tested were placed in separate, numbered 250 milliliter Erlenmeyer flasks. The numbers on the flasks correspond to numbers given to the coupons. To each flask was added the corresponding rubber coupon, a cork stopper was tightly installed and the flask was lightly swirled, and set aside for a period of two hours at a temperature of 65°–75° F. At exactly two hours for each sample and within 30 seconds time, the stopper was removed, the liquid was dumped, the coupon was shaken out onto a paper towel, blotted dry and the weight of the coupon was obtained to the nearest 0.1 milligram. The weight increase of each coupon was calculated as a percentage increase from the original weight. The liquids tested were 100 percent n-decane, 100 percent benzene and varying mixtures of these two liquids. The obtained values were corrected for the weight differences of the rubber coupons and the weight gain percentage was normalized pursuant to the equations previously described. The results are given in the FIGURE as curve 2.

EXAMPLE 2

The same test techniques of Example 1 were utilized with the exception that the liquids tested were Tichert 350, benzene and mixtures of these two liquids. Tichert 350 (a low vapor pressure nonaromatic mixture of hydrocarbons) was used for the zero point and its true value was subtracted as a blank from all the other calibration points. Benzene was used at the 100 percent point and the ratio required to bring its true value to 100 percent was applied to all the other calibration points after subtracting the blank. The rubber coupons were not corrected for their differences in weight; however, the weight increase experienced by each rubber coupon was normalized. The data is given below in Table 1 and it is plotted in the FIGURE as curve 1.

TABLE 1

| BAE Value | Normalized Weight increase |
|---|---|
| 0 | 0 |
| 1.0 | .19 |
| 2.0 | .34 |
| 4.0 | .53 |
| 8.0 | 1.29 |
| 16.0 | 3.33 |
| 25.0 | 6.96 |
| 32.0 | 10.32 |
| 40.0 | 15.85 |
| 50.0 | 22.49 |
| 64.0 | 38.82 |
| 75.0 | 52.66 |
| 85.0 | 80.84 |
| 100.0 | 100.0 |

EXAMPLE 3

Based on curve 1 of FIG. 1, the benzene aromatic equivalent content of the following compositions were determined using the techniques of Example 2. The compositions and BAE are given below in Table 2.

TABLE 2

| Tested Composition | Normalized Weight Gain % | BAE, V % |
|---|---|---|
| Toluene | 89.24 | 95.0 |
| LaBarge cutter | 1.32 | 8.1 |
| LaBarge (southwest) | 1.94 | 11.0 |
| Dalton cutter | .45 | 2.9 |
| Western cutter | 1.81 | 10.5 |
| T-350 cutter | .08 | 0.1 |
| Plateau cutter | 1.38 | 8.2 |

TABLE 2-continued

| Tested Composition | Normalized Weight Gain % | BAE, V % |
|---|---|---|
| RC-O cutter | 1.50 | 9.0 |
| Pasco cutter | 1.58 | 9.3 |
| Shale oil | .64 | 4.0 |
| Tire oil | 4.28 | 18.9 |
| Hunt oil cutter | .61 | 4.0 |

EXAMPLE 4

Using the technique of Example 1, the BAE volume percentages of six different hydrocarbon compositions were determined. These are shown in Table 3 along with the threshold limit values for the same compounds. The threshold limit values are published by the American Conference of Governmental Industrial Hygienists (May 21, 1973) and often form the basis of threshold limit values of a compound which are allowable under state laws. For example, regulatory agencies of the State of Colorado have used these values to define acceptable limits of compounds to which people can be exposed. There is an inverse relationship between the BAE values and the TLV values, which leads to a direct relationship between the BAE values and relative toxicities.

TABLE 3

| Substance | BAE, V % | TLV mg/cubic meter air |
|---|---|---|
| Benzene | 100 | 80 |
| Toluene | 95 | 375 |
| Xylene (mixed) | 83 | 435 |
| Methyl ethyl ketone | 83.7 | 590 |
| Methyl isobutyl keton | 62.9 | 410 |
| Ethyl alcohol | 0 | 1900 |

What is claimed is:

1. A method for determining the relative aromatic activity of hydrocarbon compositions comprising measuring and comparing the ability of the compositions to be sorbed by a polymeric rubber matrix.

2. The method of claim 1 wherein the rubber matrix consists of a synthetic rubber capable of sorbing aromatic hydrocarbons and which is not readily dissolved by the hydrocarbon compositions.

3. The method of claim 1 wherein the relative aromatic activity is used to determine compliance with process stream specifications defined with respect to aromatic activity.

4. The method of claim 1 wherein the aromatic activity is used to determine the compatibility of the hydrocarbon composition within a hydrocarbon mixture.

5. The method of claim 1 wherein the relative aromatic activity is used to determine the presence of an aliphatic impurity in a high purity aromatic hydrocarbon process stream.

6. The method of claim 5 wherein the relative aromatic activity is used to determine the presence of an aliphatic impurity comprising:
determining the aromatic activity of the high purity aromatic hydrocarbon stream alone;
determining the aromatic activity of the high purity aromatic hydrocarbon process stream being evaluated; and
comparing the two aromatic activities to determine the presence of an aliphatic impurity indicated by the aromatic activity of the process stream being evaluated being less than the aromatic activity of the high purity aromatic stream alone.

7. The method of claim 1 wherein the relative aromatic activity is used to determine the relative toxicities of the hydrocarbon compositions.

8. The method of claim 7 wherein the relative aromatic activity value is used to determine the toxicities of the hydrocarbon compositions comprising:
   determining the aromatic activity of the hydrocarbon compositions; and
   applying a correlation factor to the aromatic activities to obtain the toxicity of the hydrocarbon compositions wherein the correlation factor defines the relationship between the aromatic activities and the toxicity values of hydrocarbon compositions whose toxicities are known.

9. The method of claim 7 wherein the relative aromatic activity is used to determine the threshold limit values (TLV) of the hydrocarbon compositions comprising:
   determining the aromatic activity of the hydrocarbon compositions; and
   applying a correlation factor to the aromatic activities to obtain the TLV values of the hydrocarbon compositions wherein the correlation factor defines the relationship between aromatic activities and TLV values of hydrocarbon compositions whose TLV values are known.

10. The method of claim 1 wherein the relative aromatic activity is used to determine the presence of an aromatic impurity in a high purity process stream selected from the group consisting of an aqueous process stream, an aqueous process stream containing dissolved inorganic compounds, an aliphatic hydrocarbon stream and mixtures thereof.

11. The method of claim 10 wherein the process stream is an aqueous stream comprised of water.

12. The process of claim 11 wherein the relative aromatic activity is used to determine the presence of a dissolved aromatic hydrocarbon contaminant in water comprising:
   determining the aromatic activity of the water alone;
   determining the aromatic activity of the water being evaluated; and
   comparing the two aromatic activities to determine the presence of the dissolved aromatic hydrocarbon indicated by the aromatic activity of the water being evaluated being greater than the aromatic activity of the water alone.

13. The method of claim 10 wherein the process stream is an aliphatic hydrocarbon process stream.

14. The process of claim 13 wherein the relative aromatic activity is used to determine the presence of an aromatic impurity in a high purity aliphatic hydrocarbon process stream comprising:
   determining the aromatic activity of the high purity aliphatic hydrocarbon stream alone;
   determining the aromatic activity of the high purity aliphatic hydrocarbon process stream being evaluated; and
   comparing the two aromatic activities to determine the presence of an aromatic impurity indicated by an aromatic activity of the process stream being evaluated which is greater than the aromatic activity of the high purity aliphatic stream alone.

15. A method for determining the aromatic activity of a hydrocarbon composition comprising determining the aromatic equivalent (AE) value of the composition by measuring the ability of the composition, when in physical contact with a polymeric rubber matrix under standardized conditions, to cause a short term weight gain and/or swelling of the rubber matrix and comparing this value to a predetermined aromatic activity of a standard mixture to obtain the volume percent AE value.

16. A method for determining the aromatic activity of a hydrocarbon composition comprising determining the aromatic equivalent (AE) value of the composition by measuring the ability of the composition, when in physical contact with a polymeric rubber matrix under standardized conditions, to cause a short term weight gain and/or swelling of the rubber matrix, correcting the weight of the rubber matrix to a standard weight, correcting the time of exposure of the rubber matrix to the hydrocarbon composition to a standard time, then normalizing the weight gain and/or swelling measured and comparing the corrected and normalized weight gain and/or swelling to a predetermined aromatic activity of a standard mixture to obtain the volume percent AE value.

17. The method of claim 15 or claim 16 wherein the weight gain and/or swelling is used in accordance with the following equation:

$$Y = X^{\alpha X^{lnx}}$$

wherein:
   $X$ = fractional volume percent AE
   $Y$ = fractional percent of the weight gain, or the corrected and/or normalized weight gain, of the rubber matrix
   $\alpha$ = coefficient
   $\beta$ = coefficient
   ln = natural logarithm
to obtain the fractional volume percent AE value.

18. The method of claim 15 or claim 16 wherein the standardized conditions consist of a specific contact time of the rubber matrix with the hydrocarbon composition, a specific amount of the hydrocarbon composition and a temperature within a range of from about 65°–80° F. wherein the temperature and amount of hydrocarbon composition are the same as those used in obtaining the predetermined aromatic activity of the standard mixture.

19. The method of claim 15 or claim 16 wherein the rubber matrix consists of a synthetic rubber capable of sorbing aromatic hydrocarbons and which is not readily dissolved by compositions used to establish the predetermined aromatic reactivity of the standard mixture or by the hydrocarbon compositions being tested.

20. The method of claim 15 or claim 16 wherein the AE value is used to determine compliance with process stream specifications defined with respect to AE values.

21. The method of claim 15 or claim 16 wherein the standard mixture comprises mixtures of an aromatic calibration compound and a diluent calibration compound which exhibits low aromatic activity.

22. The method of claim 21 wherein the aromatic calibration compound is benzene and the AE value is the benzene aromatic equivalent (BAE).

23. The method of claim 22 wherein the weight gain and/or swelling is used in accordance with the following equation:

$$Y = X^{\alpha \beta lnx}$$

wherein:
X = fractional volume percent BAE
Y = fractional percent of the weight gain, or the corrected and/or normalized weight gain, of the rubber matrix
α = coefficient
β = coefficient
ln = natural logarithm
to obtain the fractional volume percent BAE value.

24. The method of claim 15 or claim 16 wherein the AE value is used to determine the presence of an aliphatic impurity in a high purity aromatic hydrocarbon process stream.

25. The method of claim 24 wherein AE values are used to determine the presence of an aliphatic impurity comprising:
determining the AE value of the high purity aromatic hydrocarbon stream alone;
determining the AE value of the high purity aromatic hydrocarbon process stream being evaluated; and
comparing the two AE values to determine the presence of an aliphatic impurity indicated by the AE value of the process stream being evaluated being less than the AE value of the high purity aromatic stream alone.

26. The method of claim 25 where the relative aromatic activity is used to determine the compatibility of a hydrocarbon composition within a hydrocarbon mixture to formulate a stable product comprising:
determining a range of acceptable aromatic activity by empirically determining the aromatic activity of known hydrocarbon compositions having desired characteristics of the product to be formulated;
determining the aromatic activity of the potential hydrocarbon composition to be incorporated into the hydrocarbon mixture;
selecting the hydrocarbon composition having an aromatic activity within the acceptable range of aromatic activity values; and
incorporating the hydrocarbon composition into the hydrocarbon mixture to form a stable product.

27. The method of claim 15 or 16 wherein the AE value is used to determine the compatibility of a hydrocarbon composition within a hydrocarbon mixture.

28. The method of claim 27 wherein the AE value is used to determine the compatibility of a hydrocarbon composition within a hydrocarbon mixture to formulate a stable product comprising:
determining a range of acceptable AE values by empirically determining the AE values of known hydrocarbon compositions having desired characteristics of the product to be formulated;
determining the AE values of the potential hydrocarbon composition to be incorporated into the hydrocarbon mixture;
selecting the hydrocarbon composition having an AE value within the acceptable range of AE values; and
incorporating the hydrocarbon composition into the hydrocarbon mixture to form a stable product.

29. The method of claim 27 wherein the AE value is a benzene aromatic equivalent.

30. The method of claim 15 or 16 wherein the AE value is used to determine the presence of an aromatic impurity in a high purity process stream selected from the group consisting of an aqueous process stream, an aqueous process stream containing dissolved inorganic compounds, an aliphatic hydrocarbon process stream and mixtures thereof.

31. The method of claim 30 wherein the process stream is an aqueous process stream.

32. The process of claim 31 wherein AE values are used to determine the presence of a dissolved aromatic hydrocarbon contaminant in water comprising:
determining the AE value of the water alone;
determining the AE value of the water being evaluated; and
comparing the two AE values to determine the presence of the dissolved aromatic hydrocarbon indicated by the AE value of the water being evaluated being greater than the AE value of the water alone.

33. The process of claim 30 wherein the process stream is an aliphatic hydrocarbon process stream.

34. The method of claim 33 wherein the AE value is used to determine the presence of an aromatic impurity in a high purity aliphatic hydrocarbon process stream comprising:
determining the AE value of the high purity aliphatic hydrocarbon stream alone;
determining the AE value of the high purity aliphatic hydrocarbon process stream being evaluated; and
comparing the two AE values to determine the presence of an aromatic impurity indicated by an AE value of the process stream being evaluated which is greater than the AE value of the high purity aliphatic stream alone.

35. The method of claim 30 wherein the AE value is a benzene aromatic equivalent.

36. The method of claim 15 or 16 wherein the AE value is used to determine the relative toxicity of the hydrocarbon composition.

37. The method of claim 36 wherein the AE value is used to determine the toxicity of the hydrocarbon composition comprising:
determining the AE value of the hydrocarbon composition; and
applying a correlation factor to the AE value to obtain the toxicity of the hydrocarbon composition wherein the correlation factor defines the relationship between AE values and toxicity values of hydrocarbon compositions whose toxicities are known.

38. The method of claim 37 wherein the AE value is a benzene aromatic equivalent.

39. The method of claim 36 wherein the AE value is used to determine the threshhold limit value (TLV) of a hydrocarbon composition comprising:
determining the AE value of the hydrocarbon composition; and
applying a correlation factor to the AE value to obtain the TLV value of the hydrocarbon composition wherein the correlation factor defines the relationship between AE values and TLV values of hydrocarbon compositions whose TLV values are known.

40. The method of claim 39 wherein the AE value is a benzene aromatic equivalent.

* * * * *